(12) United States Patent
Miethe et al.

(10) Patent No.: US 6,488,894 B1
(45) Date of Patent: Dec. 3, 2002

(54) DEVICE FOR SEQUENTIAL DISCHARGE OF FLOWABLE REAGENTS

(75) Inventors: Peter Miethe, Schleberoda (DE); Dimitri Plaksine, Juelich (DE); Elena Gromakovskaja, Juelich (DE)

(73) Assignee: Biognosis GmbH (DE)

( * ) Notice: Subject to any disclaimer, the term of this patent is extended or adjusted under 35 U.S.C. 154(b) by 0 days.

(21) Appl. No.: 09/554,753

(22) PCT Filed: Nov. 19, 1998

(86) PCT No.: PCT/EP98/07413

§ 371 (c)(1), (2), (4) Date: Jul. 7, 2000

(87) PCT Pub. No.: WO99/25475

PCT Pub. Date: May 27, 1999

(30) Foreign Application Priority Data

Nov. 19, 1997 (DE) .......................................... 197 51 327
Jun. 6, 1998 (DE) .......................................... 198 25 362

(51) Int. Cl.⁷ .............................. B01L 3/00; B01L 3/02; G01N 21/00; G01N 31/22; G01N 15/06; G01N 33/00; F16K 43/00; F16K 51/00; B65D 25/08; B67D 5/00; B67D 3/00

(52) U.S. Cl. .................... 422/100; 422/99; 422/102; 422/68.1; 422/58; 422/61; 436/180; 73/864; 73/864.01; 73/864.11; 73/864.16; 137/318; 137/197; 206/219; 222/5; 222/81; 222/82; 222/544

(58) Field of Search .......................... 422/99, 100, 61, 422/65, 57, 68.1, 102, 58; 73/864, 864.01, 864.11, 864.13, 864.16; 222/5, 81, 82, 544; 137/197, 318; 206/219; 436/180

(56) References Cited

U.S. PATENT DOCUMENTS

| | | | | |
|---|---|---|---|---|
| 3,036,894 A | * | 5/1962 | Forestiere | 206/484 |
| 3,600,953 A | * | 8/1971 | Isreeli et al. | 422/82 |
| 3,666,420 A | * | 5/1972 | Paatsch | 137/240 |
| 3,713,779 A | * | 1/1973 | Sirago et al. | 206/219 |
| 3,743,103 A | * | 7/1973 | Isreeli et al. | 210/532.1 |
| 4,916,078 A | * | 4/1990 | Klose et al. | 422/102 |
| 4,943,522 A | | 7/1990 | Eisinger et al. | |
| 4,999,164 A | * | 3/1991 | Puchinger et al. | 422/100 |
| 5,073,484 A | * | 12/1991 | Swanson et al. | 422/56 |
| 5,154,888 A | * | 10/1992 | Zander et al. | 206/219 |
| 5,156,811 A | * | 10/1992 | White | 210/416.1 |
| 5,268,147 A | * | 12/1993 | Zabetakis et al. | 422/68.1 |
| 5,288,463 A | * | 2/1994 | Chemelli | 422/102 |
| 5,290,518 A | * | 3/1994 | Johnson | 422/101 |
| 5,387,526 A | * | 2/1995 | Garner et al. | 356/244 |
| 5,399,497 A | * | 3/1995 | Kumar et al. | 422/68.1 |
| 5,496,523 A | * | 3/1996 | Gazit et al. | 422/100 |
| 5,955,032 A | * | 9/1999 | Kelly et al. | 422/100 |
| 6,221,655 B1 | * | 4/2001 | Fung et al. | 422/101 |
| 6,284,549 B1 | * | 9/2001 | Guthrie | 137/197 |

* cited by examiner

Primary Examiner—Jill Warden
Assistant Examiner—Brian R Gordon
(74) Attorney, Agent, or Firm—Diller, Ramik & Wight

(57) ABSTRACT

The invention relates to a device in which at least two liquid or semi-liquid reagents can be stored separately. When used, the inventive device enables precise, chronologically defined, sequential reagent discharge in a reaction chamber by means of a linear movement without any prior mixing of said reagents.

12 Claims, 4 Drawing Sheets

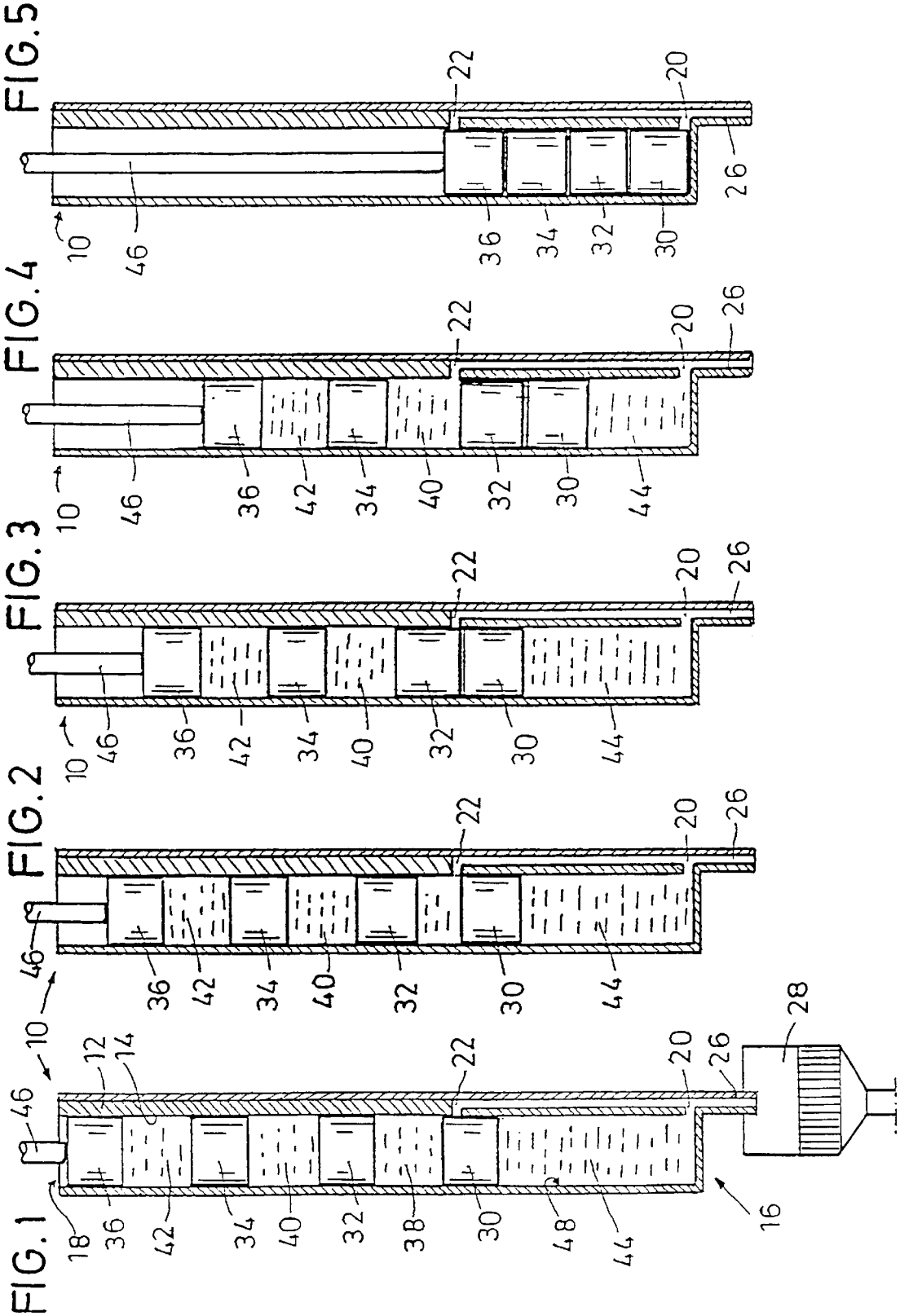

DEVICE FOR SEQUENTIAL DISCHARGE OF FLOWABLE REAGENTS

This is a 371 of International Application No. PCT/EP98/07413 filed Nov. 19, 1998.

BACKGROUND OF THE INVENTION

The present invention refers to a device allowing to store a plurality of liquid or semi-liquid (flowable) reagents, required for a given chemical or biochemical synthetic or test reaction, in integrated form, i.e. in a single container that is easy to produce and to handle, and, in use, the device further allowing for an exact dosing of such reagents in a reaction chamber without any prior mixing of the reagents by a simple linear movement of a plunger.

Integrated storage and defined dosing of a plurality of liquid or semi-liquid reagents is of great importance for the production of ready-to-use chemical and pharmaceutical products which are chemically complex, i.e. wherein various, sometimes very different reagents that react with each other have to be supplied in doses into a reaction chamber in a chronologically defined sequence, and which also must be easy to produce and to handle by the user. A sufficiently simple handling is realized in particular when the user can trigger the dosing by only a few unmistakable manipulations.

Important fields of application are the chemical and biochemical fast analytics and in active substance formulating for pharmaceutical purposes. Clinical fast analytics is of particular commercial importance. Here, simple integrated systems are needed that operate reproducibly and, possibly, quantitatively, which can be used in decentral applications (doctor's offices, pharmacies, households) even by non-skilled users. A typical list of requirements concerning the handling and reliability has been established In the US in the guidelines to the CLIA (clinical laboratory improvement act).

A device presently used in fast analytic for storing and dosing of a maximum of three different reagents is described In U.S. Pat. No. 4,943,522. Here, a biochemically active component is applied to a strip-shaped glass tissue and dried thereon. Dried, it can be stored over a longer period. The glass tissue is placed over a strip of cellulose nitrate. In use, a liquid sample is applied that penetrates the glass tissue due to capillary forces acting and dissolves the reagents stored there, thus initiating a partial reaction. The reaction mixture will then penetrate further Into the cellulose nitrate membrane, where a second and, possibly, a third reactive component is present reacting further with the sample. This method is not practical for reactions requiring more than three reagents, since, in general, mixing an/or netting reactions between the components occur that are difficult to control. Intermediate washing steps to avoid these effects are not possible. Specifically, the device does not provide a very good quantitative evaluation since the basic phyisco-chemical steps such as drying, reconstitution and lateral diffusion are very sensitive to interferences and cannot well be reproduced without great technical effort. Therefore, preference is given to liquid reagents. A corresponding device for storing and dosing is described in WO/A/9718895. It Is based on the use of at least two rigid storage receptacles/containers holding the reagents. The containers are disposed one behind the other and are each closed at the bottom by means of a closing means that can be opened through a trigger means. In use, the reagents flow through the open bottoms due to gravity and into the underlying container and from the last container out from the device and into the reaction chamber. On principle, the dosing may be performed in two ways. Either, the closing means of the individual containers are opened sequentially, starting with the container nearest the outlet opening to the reaction chamber, the higher container being opened only when the lower container is empty, or all containers are opened simultaneously with liquids from higher containers flowing into a lower container not yet empty. In the first case, a multiple triggering of the dosing is necessary. This is tedious to the user and not acceptable for many applications. In the second case, partial mixing cannot be excluded. Generally, this leads to uncontrollable pre-reactions or dilution. The above application suggests to minimize these effects by neutral additives that change the density and the viscosity of the liquids. However, this does not exclude reactions at phase interfaces and mixing caused by microturbulences.

Another disadvantage of the above device is the control of the dosing by gravity in combination with the flow resistance of the application device and, possibly, the connected reaction chamber. Since the flow resistance within the containers depends very strongly on the interfacial tensions of the liquids, small added amounts of surface active substances, e.g., can have strong effects on the flow characteristics. In applications where, for reaction-kinetic reasons, a reproducible outflow behavior of the reagents is required, this causes very large variations in the course of the reaction.

SUMMARY OF THE INVENTION

It is an object of the present invention to provide a device which enables, in a simple manner, a precise, chronologically defined and sequential discharge of at least two liquid or semi-liquid reagents into a reaction chamber by a single mechanical linear movement, without prior mixing of the reagents, According to the present invention, a device is employed wherein the individual reagents are disposed one behind the other in the form of a reagent column, the individual reagents segregated by movable partitions that are slidably supported in a sealing manner at the inner surface of a cylindrical container holding the reagent column.

For dosing, the segregated reagent column is advanced towards and through an outlet opening, the reagents leaving the container accordingly and the partitions being advanced into a portion of the container that is below the inlet opening of the outlet channel. Here, the media contained in this portion of the container is pushed either into the environment or into the reaction chamber via a pressure compensation channel. In the first instance, the pressure compensation channel is open to the environment and the media is air. In the second instance, the pressure compensation channel is open to the reaction chamber and the media is a liquid to be dosed, e.g. a washing solution.

Further, a holding force generating unit is integrated in the device, which, together with the first lower partition, seen in the discharge direction, generates a pressure counteracting the linear movement and higher than the pressure generated by the pressure generating unit. Here, it is possible, for example, to provide a spring between the bottom of the receiving container and the first partition. A particularly simple solution is to use a first partition having a slightly higher friction that the subsequent partitions, due to a larger outer diameter. An analogous effect may be obtained if the receiving portion below the inlet opening of the outlet channels has a slightly smaller inner diameter, e.g., by 1–10%, than the superjacent portion of the receiving chamber, or if it has a higher friction due to special surface treatment.

In an advantageous development of the invention, it is provided that the pressure generating unit is a plunger or rod abutting the inner surface of the receptacle in a sealing manner and being slidable towards the first end of the receiving chamber. Since the topmost reagent volume in the reagent column is usually sealed off by a partition element, this partition element acts as a plunger onto which the rod of a pressure generating device acts. The pressure generating device may also be designed as a pneumatic pressure generating unit acting pneumatically on the topmost partition element. Hydraulic systems are also conceivable as the pressure generating unit.

Suitably, the outlet opening is joined by an outlet channel which extends beyond the first end of the receptacle. This outlet channel is disposed either outside or within the receiving chamber. When disposed within, it is designed as an outlet tubule whose end arranged in the receiving chamber can pierce the partition elements when these move towards the first end of the receptacle due to the pressure exerted by the pressure generating unit. Here, the outlet tubule directed opposite to this direction of movement.

Should the portion of the receiving chamber between the outlet opening and the relief opening merely hold air or a gas, it is suitable to direct the relief opening into the environment around the receptacle. It is also possible that a reagent is present in this portion of the receiving space. It is then suitable to have the relief opening in fluid communication with the outlet opening, for example, by making the relief opening terminate in the outlet channel.

Specifically, the holding force generating device is a unit increasing the friction between the lowermost partition element in an area between the outlet opening. The increased static friction thus obtained guarantees that at least the lowermost partition element is not moved any further when reaching the portion of the receiving chamber below the outlet opening, so that the pressure accumulated by the pressure generating unit is used to discharge the reagent above the lowermost partition element through the outlet opening. When the next partition element comes into the vicinity of the outlet opening and closes the same, the pressure from the pressure generating device will move the two overlying partition elements towards the first end of the receiving chamber until the upper one of these two partition elements is situated below the outlet opening. Now, the reagent of the volume above this partition element may flow off through the outlet opening. This process is repeated corresponding to the number of partition elements and reagent volumes.

Increased friction in the portion below the outlet opening of the receiving chamber may, for example, be effected by a corresponding treatment of the contacting surfaces of the lowermost partition element and the inner surface of the receiving chamber. It is also conceivable to provide a constriction in a portion of the receiving chamber below the outlet opening or to configure the lowermost partition element oversized with respect to the other partition elements, i.e. wider than the other partition elements. Finally, it is also conceivable to use a spring as the holding force generating unit whose resilience acts opposite to the direction of the partition elements along which these move under the action of the pressure from the pressure generating unit.

In this variant of the invention, the partitions are replaced with gas or liquid volumes. These gases or liquids are inert and substantially not miscible with the reagents. The liquids are hydrophobic. In the outlet opening, there is a hydrophilic membrane allowing only the reagents to pass but not the hydrphobic separating liquids or the gaseous separating volumes. In the initial state of the device according to this variant, a closure is arranged in the region of the outlet device dosing the same from inside. The use of liquid or gas volumes for separation requires the receptacle to be configured as a capillary. This capillary is open at its two opposite ends and has a branch adjoining the outlet opening.

Below the outlet opening, between the same and the lower first end of the capillary, the holding force generating device, already mentioned in connection with the partition elements of the first variant of the invention, is provided, now cooperating with the closure. Therefore, all above explanations regarding the holding force generating device apply analogously to the second variant of the invention.

The following is a detailed discussion of embodiments of the invention with reference to the drawings.

BRIEF DESCRIPTION OF THE DRAWINGS

FIGS. 1 to 5 illustrate the different operational states of a discharge device according to a first embodiment;

DESCRIPTION OF THE PREFERRED EMBODIMENTS

Figures 6, 7, 8, 9:
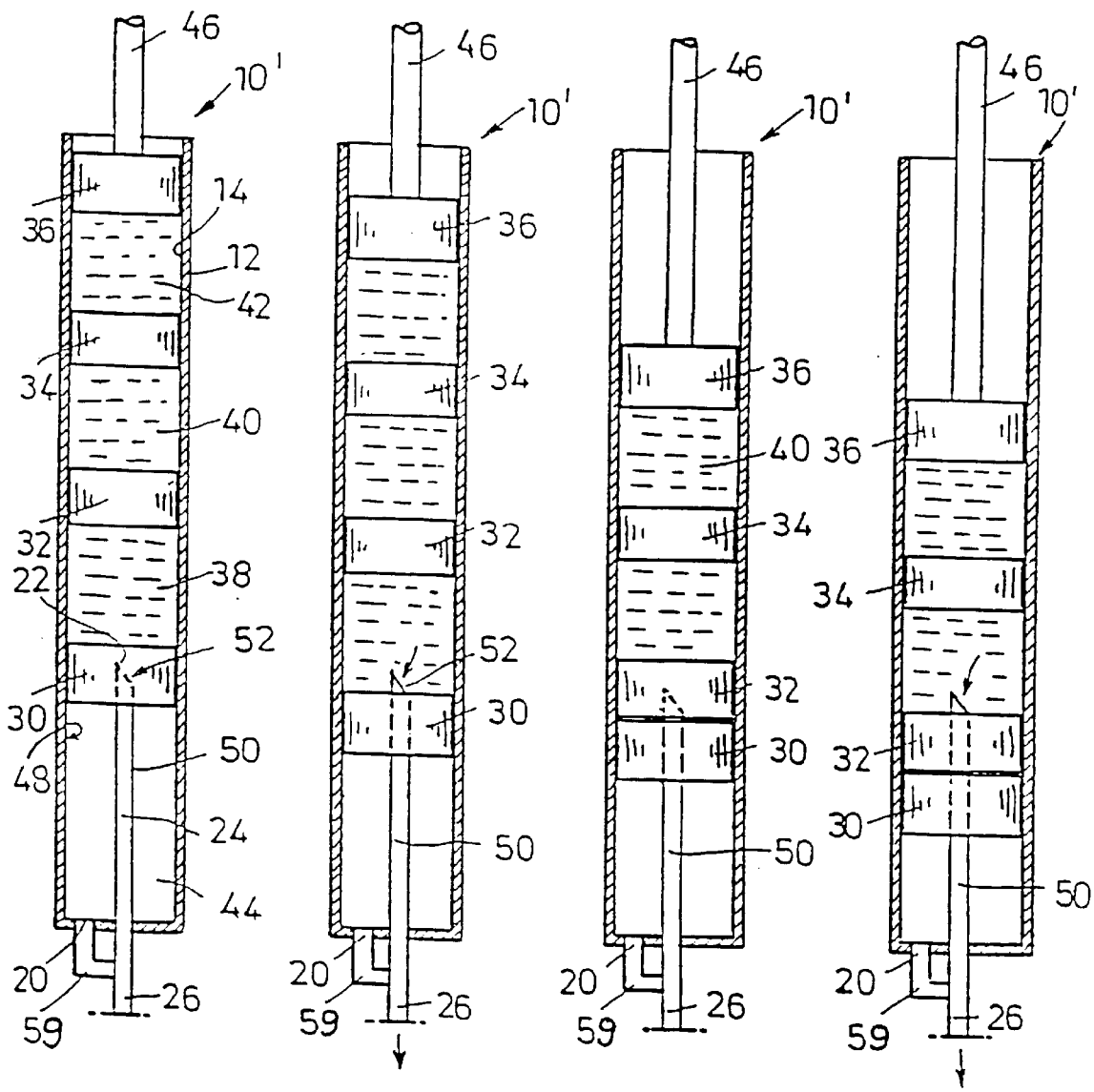
FIGS. 6 to 9 illustrate the different operational states of a discharge device according to a second embodiment.

FIGS. 1 to 5 illustrate a first embodiment of a discharge device 10. The discharge device 10 comprises a substantially tubular receptacle 12, the receptacle 12 is formed with a substantially cylindrical receiving chamber 14 with a lower first end 16 and an upper second end 18. The lower end 16 is provided with a radially oriented relief opening 20. Above this relief opening 20, an outlet opening 22 is provided in the sidewall of the receptacle 12. Both openings are communicated through an outlet channel 24. This outlet channel 24 terminates in an outlet pipe 26 ending above a reaction chamber illustrated at 28.

In the present instance, four piston-like partition elements 30, 32, 34, 36 of elastomer material are spaced from each other in the receiving chamber 14. Reagent volumes 38, 40, 42 exist between adjacent partition elements. Moreover, a reagent is also present in the region between the lower first end 16 of the receiving chamber and the lowermost partition element 30. This reagent volume is indicated at 44 in FIGS. 1 to 5.

In the initial state of the device 10, illustrated in FIG. 1, the lowermost partition element 30 is located on the level of the outlet opening 30, there is the reagent column with the intermediate partition elements 32, 34, 36. The lowermost partition element 36 is acted upon by a pressure generating unit in the form of a plunger 46 adapted to be moved downward. When this plunger that is located at the upper second end 18 of the receiving chamber 14, is moved towards the first lower end 16 of the receiving chamber 14, the four partition elements 30–36 are also moved downward. In the process, liquid exits from the reagent volume 44 via the relief opening 20 and the outlet pipe 26. This process continues until the lower partition element 30 has reached the position immediately below the outlet opening 22, as illustrated in FIG. 2. Thus, the outlet opening 22 is cleared so that reagent may flow out from the volume 38 through the outlet opening 22 and the outlet channel 24. The lowermost partition element 30 is held in its position immediately below the outlet opening 22 under action of a holding force generating device 48 that consists of a constriction of the receiving chamber portion between the outlet opening 22 and the lower first end 16. This constriction may, for example, be realized by slightly protruding ribs (not illustrated). As an alternative, it is possible for the lowermost partition element 30 to be oversized. In any case, the goal is that the lowermost partition element 30, after having passed the outlet opening 22, is not moved further towards the lower end 16 due to the static liquid pressure accumulated by the pressure generating device 46 so that reagent liquid may exit from the outlet opening 22.

This process continues until the second partition element 32 closes the outlet opening 22 and afterwards contacts the lowermost partition element 30, as illustrated in FIG. 3. Now, these two partition elements 30, 32 are moved together towards the first end until the partition element 32 has passed the outlet opening 22 completely and has cleared the same (see FIG. 4). Now reagent may emerge from the volume 40. The process described above is repeated in correspondence to the number of reagent volumes or partition elements. In the final state, the situation illustrated in FIG. 5 occurs, for example.

A second embodiment of the device 10' will now be explained with reference to FIGS. 6 to 9. Individual elements of the device 10' corresponding to those of the device 10 have been denoted by the same reference numerals.

As with the embodiment in FIGS. 1 to 5, the receptacle 12 of the device 10' is filled with a reagent column comprised of reagent volumes 38–44 and separating movable partition elements 30–36. The outlet channel is designed as a rigid tubule 50 with a first end 52 located in the receiving chamber 14 and extending to its other end forming the outlet pipe 26 outside the receptacle 12. The relief opening 20 is connected with the tubule 50 via a communication line 59. The individual partition elements 30–36 can be penetrated by the tubule 50.

In the storage condition, the outlet opening 22 formed by the end 52 of the tubule 50 is closed by the lowermost partition element 30 and blocked. In this state, the reagents can be stored without the risk of mixing or flowing out. In use, the plunger 46 exerts a force on the uppermost partition element 36 so Fat the reagent column moves towards the relief opening 20. In doing so, the lowermost partition element 30 is "pierced" by the tubule until the lower partition element 30 has moved past first end 52 of the outlet tubule 50, thereby clearing the outlet opening 22. Now reagent may flow from the volume 38 through the outlet channel 24 and be discharged (see FIG. 7). This process continues until the next partition element 32 contacts the first end 52 of the outlet tubule 50, thereby again closing the outlet opening (see FIG. 8). Both lower partition elements 30, 32, which are now contacting each other, are moved downwards together when the plunger 46 is depressed further, until the situation depicted in FIG. 9 occurs, where the upper partition element 32 has moved past the end 52 of the outlet tubule 50 so that now reagent can be discharged from the volume 40 through the outlet tubule 50. Every time the lowermost partition element 30 is pressed down, reagent escapes from the volume 44 through the relief opening 20. As such, the device 10' is functionally analogous to the device 10, only the sealing mechanism and the clearing mechanism for the outlet opening 22 being different.

Figure 10:
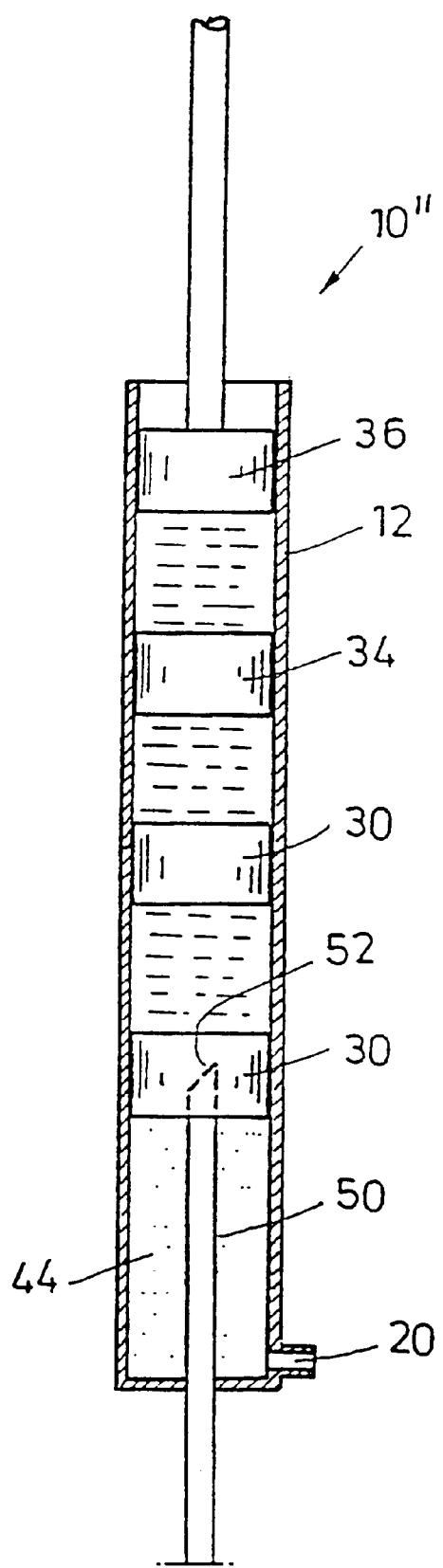
FIG. 10 is a representation of a third embodiment of the discharge device.

FIG. 10 illustrates a third embodiment of a device 1" for sequentially discharging flowable reagents. This embodiment is almost identical to the one in FIGS. 6 to 9. The only difference is that the relief opening 20 is not connected with the outlet tubule 50 but opens to the environment of the receptacle 12. The volume 44 now holds gas (air) discharged to the environment when the partition elements 30–36 are pushed into the region below the end 52 of the outlet tubule 50.

Figure 11:
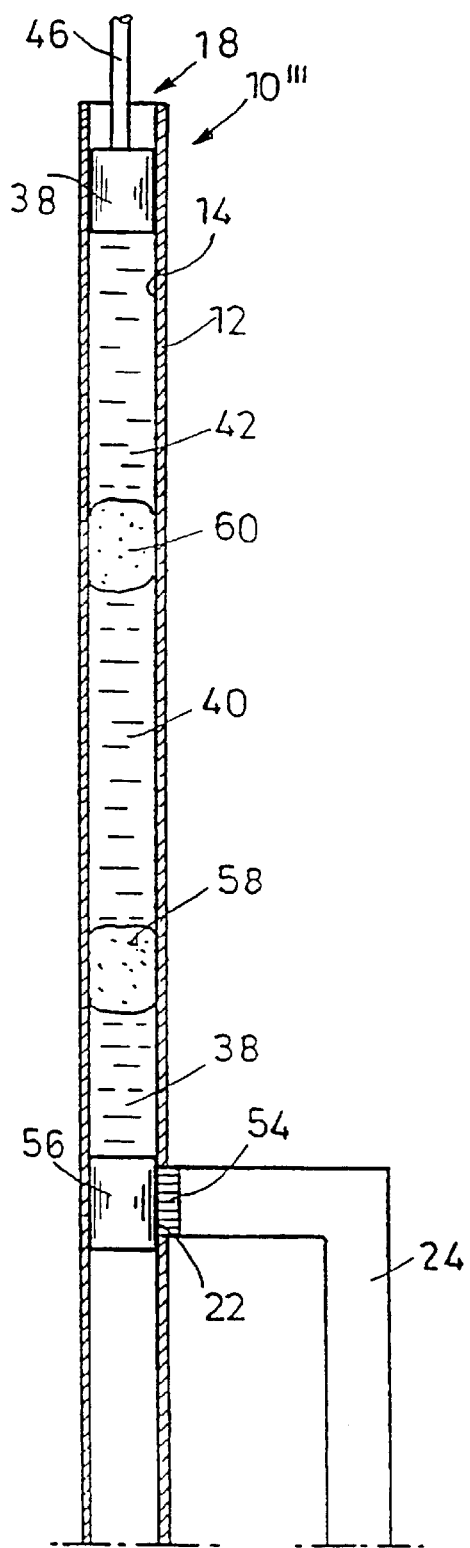
FIGS. 11 and 12 illustrate different operational states of a discharge device according to a another embodiment.
Figure 12:
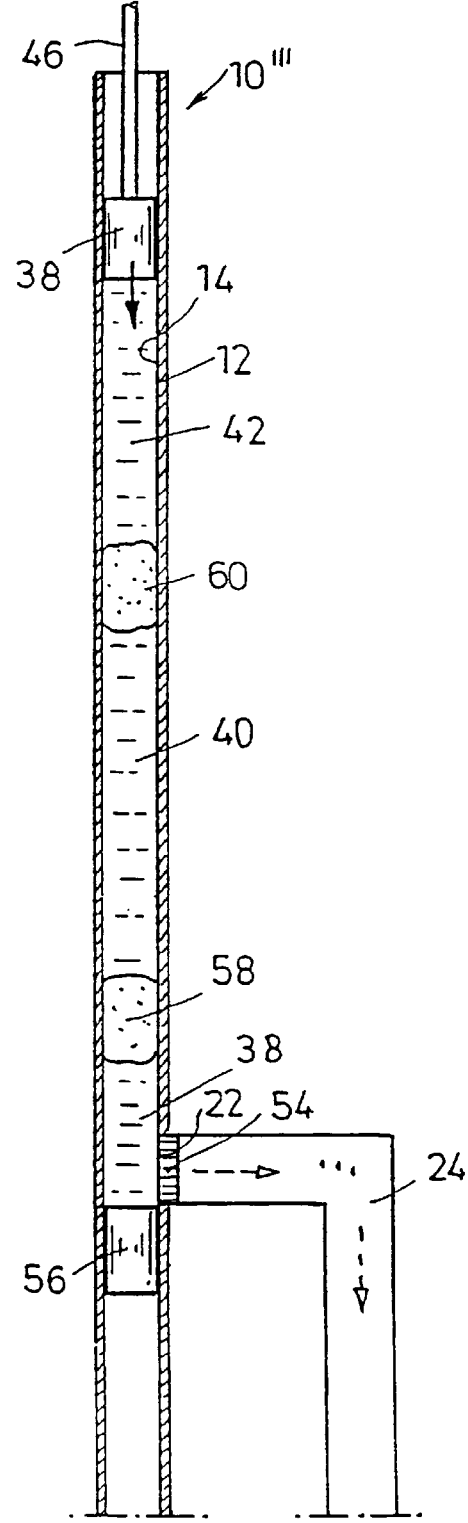

FIGS. 11 and 12 illustrate a fourth embodiment of a device 10''' for sequentially discharging flowable reagents. In this instance, the receptacle 12 is a capillary whose lumen forms the receiving chamber 14. The capillary is open at the top and bottom ends 16, 18. The lower end acts as a relief opening 20.

Above the lower end 18, the wall of the capillary is provided with a radial outlet opening 22 filled by a hydrophilic membrane 54. Adjoining the outlet opening 22 is the outlet channel 24. Within the capillary 12, a closure member 56 is located in the initial state of the device''', the member covering and thus dosing the outlet opening 22 and the hydrophillc membrane 54 from inside. Above the closure member 56, the reagent volumes 38, 40, 42 are located which are separated by gas bubbles or volumes of hydrophobic liquids 58, 60. Using a plunger 36, corresponding to the partition element 30 of the previous embodiments, hydrostatic pressure may be applied from above to the reagent column by means of the plunger. Due to this pressure, the entire reagent column, together with the closure member 56, moves towards the bottom end 16 of the capillary 12. The downward movement of the closure member 56 continues until the outlet opening 22 is opened far enough for reagent to flow through the membrane 54 from the volume 38 above the closure member and through the outlet channel 24. Since the membrane 54 is hydrophilic, it allows the reagent of volume 38 pass. After all reagent has flown from volume 38, the lowermost gas or liquid volume 58 arrives in the area of the opening 22 and thus the membrane 54. Since the volume 58 is hydrophobic, it cannot pass the membrane 54. As a consequence, volume 58 travels on at the opening 22 and the membrane 54 within the capillary 12 towards the lower end 16, together with the closure member 56. Thereafter, i.e. after clearing the membrane 54, the same is contacted by the reagent of the next reagent volume 40, the membrane 54 again allowing the reagent to pass because of its hydrophilic properties. In the manner described above, the device 10''' can be used to sequentially dose the reagents and avoid mixing thereof.

We claim:

1. A device for sequentially discharging flowable reagents, comprising:

a receptacle comprising a receiving chamber with two opposite ends, the receptacle having a relief opening at the first end of the receiving chamber, a pressure generating unit adapted to be positioned or arranged at the receptacle at the second end of the receiving chamber, and adapted to build pressure in the receiving chamber, a reagent column contained in the receiving chamber, comprising at least two reagent volumes separated by a respective partition element, each partition element abutting the inside of the receptacle in a sealing manner and being slidable into the receiving chamber towards the first end thereof, an outlet opening arranged at a branch between the first and the second end of the receiving chamber, the distance between the outlet opening and the relief opening being at least as great as the thickness of the first partition element between the outlet opening and the second end of the receiving chamber, a holding force generating unit arranged in the region between the outlet opening and the relief opening in the receiving chamber, for generating a holding force acting at least on the partition elements within this region of the receiving chamber, which is great enough to cause a high flow resistance to the reagents in this region that is higher than the resistance occurring when the reagents flow out from the outlet opening.

2. The device of claim 1, wherein the pressure generating unit comprises a plunger abutting the inside of the receptacle in a sealing manner and being slidable towards the first end of the receiving chamber.

3. The device of claim 1 or 2, wherein an outlet channel is provided extending outside the receiving chamber and being connected to the receiving chamber through the outlet opening.

4. The device of claim 2 or 3, wherein the relief opening is communicated with the outlet channel.

5. The device of one of claims 1 to 4, wherein the holding force generating unit is a unit increasing the friction of at least the lowermost partition element in the area of the outlet opening and the relief opening as compared to the remainder of the receiving chamber.

6. The device of claim 5, wherein the holding force generating unit is a constriction in the portion of the receiving chamber between the outlet opening and the relief opening.

7. The device of claim 5, wherein the holding force generating unit is an enlargement of the lowermost partition element making the same wider than the other partition elements.

8. The device of claim 5, wherein the increase in friction is obtained by a corresponding structure of the contacting surfaces of the lowermost partition element and the receiving chamber.

9. The device of one of claims 1 to 4, wherein the holding force generating unit is a spring whose resilience acts opposite to the direction of movement of the at least one partition element when the pressure generating unit acts thereupon.

10. The device of claim 2, wherein an outlet channel is provided extending outside the receiving chamber and being connected to the receiving chamber through the outlet opening.

11. The device of claim 2, wherein an outlet tubule having an outlet channel is provided, which extends in the direction of movement of the at least one partition element and extends from outside the receiving chamber into the same, and whose end located in the receiving chamber forms the outlet opening of the receiving chamber, and wherein the at least one partition element can be pierced by the outlet tubule.

12. The device of claim 3, wherein the relief opening is communicated with the outlet channel.

* * * * *